US006303847B1

United States Patent
Kawaoka et al.

(10) Patent No.: US 6,303,847 B1
(45) Date of Patent: Oct. 16, 2001

(54) DNA ENCODING A TRANSCRIPTION FACTOR CONTROLLING PHENYLPROPANOID BIOSYNTHESIS PATHWAY

(75) Inventors: Akiyoshi Kawaoka; Hiroyasu Ebinuma, both of Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 09/282,146

(22) Filed: Mar. 31, 1999

(30) Foreign Application Priority Data

Mar. 31, 1998 (JP) .................................................. 10-125171

(51) Int. Cl.$^7$ ............................... A01H 5/00; C12N 5/14; C12N 15/29; C12N 15/82
(52) U.S. Cl. ....................... 800/298; 435/320.1; 435/419; 536/23.6
(58) Field of Search ................................ 435/69.1, 320.1, 435/419, 468; 536/23.6; 800/278, 286, 298

(56) References Cited

PUBLICATIONS

Baltz R, et al. "Characterization of a pollen–specific cDNA from sunflower encoding a zinc finger protein" Plant J. 2: 713–721 (Abstract Only). 1992.*

\* cited by examiner

*Primary Examiner*—Amy J. Nelson
(74) *Attorney, Agent, or Firm*—Oblon, Spivak, McClelland, Maier & Neustadt, P.C.

(57) ABSTRACT

The present invention relates to an isolated and purified DNA having a nucleotide sequence which comprises SEQ ID NO:1, and encodes a transcription factor controlling a phenylpropanoid biosynthesis pathway; a recombinant vector comprising the DNA; the recombinant vector, further comprising a promoter to which the DNA is operably fused; the recombinant vector, wherein the DNA is operably fused to the promoter in the sense or antisense direction; a plant cell into which the DNA has been introduced; a plant regenerated from the plant cell; and an isolated and purified DNA which encodes a protein having the amino acid sequence of SEQ ID NO:2.

9 Claims, 1 Drawing Sheet

FIG. 1 ter: NOPALINE SYNTHASE TERMINATOR

FIG. 2 mini: CaMV35S PROMOTER FRAGMENT
(PORTION FROM TRANSCRIPTION
INITIATION POINT TO 90 bp)

FIG. 3

DNA ENCODING A TRANSCRIPTION FACTOR CONTROLLING PHENYLPROPANOID BIOSYNTHESIS PATHWAY

BACKGROUND OF THE INVENTION

1. Field of the Invention

The present invention relates to techniques for controlling the expression of genes relating to biosynthesis of phenylpropanoid.

2. Description of the Background

With the advance of plant molecular biology in recent years, it has become possible to breed plants having useful characteristics, such as resistance to disease and insect damage or resistance to a herbicide, by using a sense gene or anti-sense gene. That is, the expression of a desired characteristic can be promoted or suppressed by linking, in a sense direction or anti-sense direction, a gene relating to the expression of the desired characteristic with a promoter permitting the expression in a plant to form a chimeric gene, and introducing the resulting chimeric gene to a plant as a vector. Based on such a technique, for example, a plant resistant to disease and insect damage to which an insecticidal BT toxin gene derived from *Bacillus thuringensis* has been introduced in a sense direction (D. A. Fischhoff et al., *Bio/Technology*, 232: 738–743 (1987)) and an excellent storable tomato to which a polygalacturonase gene relating to over-ripening of tomato fruit has been introduced in an anti-sense direction (C. J. Smith et al., Nature, 334: 724–727 (1988)) have been produced.

When such a technique is used, the expression of the desired characteristic is promoted in a plant to which a sense gene (a gene which expresses a desired characteristic and is fused to a promoter in a sense direction) has been introduced; on the other hand, the expression of the desired characteristic is inhibited in a plant to which an anti-sense gene (the same gene as the sense gene, which is fused to a promoter in an anti-sense direction) has been introduced. The expression of the desired characteristic is suppressed by the introduction of an anti-sense gene because in a plant cell, RNA synthesized from the anti-sense gene as a template is complementarily bound to mRNA derived from a gene of the plant itself relating to the expression of the desired characteristic to inhibit the subsequent synthesis of protein.

However, many genes of a plant form a multi-gene family and genes belonging to such a family show a high homology in a nucleotide sequence respectively. Even if the expression of such a gene belonging to a multi-gene family is controlled using the anti-sense method, the RNA of the anti-sense gene is inevitably bound at random to the mRNAs of many other genes belonging to the same family to control their expression, which makes it impossible to control the expression of only the desired gene, so that various characteristic suppression patterns is caused. Thus, the results are sometimes quite different from those as expected.

Also, the phenylpropanoid biosynthesis pathway is a complicatedly branched reaction system which exists specifically in plants and it relates to the biosynthesis of components of a cell wall (for example, lignin, suberin), pigments of a flower, antibacterial substances and the like. Phenylpropanoid derivatives available through such a biosynthesis pathway can also be used for UV protecting agents, insecticides or the like. If the expression of a gene relating to this phenylpropanoid biosynthesis pathway can be promoted or suppressed accurately, it becomes possible to control this biosynthesis pathway to produce a tree containing a lignin at a low content or carry out mass production of useful substances. In this case, however, it is difficult to control the expression of the gene by the anti-sense method owing to the above-described problem in homology between genes. For example, it is reported that a transformed plant to which a gene of phenylalanine ammonia lyase (PAL) or peroxidase (PRX) which is an enzyme acting in the phenylpropanoid biosynthesis pathway had been introduced in an anti-sense direction exhibited diversified controlling effects such as growth inhibition (M. M. Campbell and R. R. Sederoff, *Plant Physiol.*, 110: 3–13 (1996)) and a change in a lignin content of tobacco to which a caffeic acid O-methyltransferase gene had been introduced in an anti-sense direction was not so large as expected (W. Ni et al., *Transgen. Res.*, 3: 120–126 (1994)).

SUMMARY OF THE INVENTION

In consideration of the above-described problems, an object of the present invention is to provide a DNA and a vector which can accurately promote or suppress the expression of a specific gene relating to the phenylpropanoid biosynthesis pathway of a plant.

With a view toward overcoming the above-described problems, the present inventors have carried out an extensive investigation. As a result, the inventors paid attention to the fact that in the 5'-upstream non-translated region of specific genes relating to the phenylpropanoid biosynthesis pathway, for example, a cynnamyl alcohol dehydrogenase (CAD) gene, chalconic acid synthetase (CHS) gene, 4-coumaric acid CoA ligase (4CL) gene, PAL gene and PRX gene, there exist sequences controlling the expression of these genes, and these sequences have a very high homology between these genes. So the inventors isolated a factor promoting the transcription of these genes by binding to these sequences (hereinafter referred to as a "transcription factor") and then introduced a DNA encoding the factor into a plant as a sense gene or anti-sense gene so that the expression of the above-described gene can be accurately promoted or suppressed. Thus, the present invention has been completed.

Specifically, the above and other objects of the present invention may be accomplished by an isolated and purified DNA having a nucleotide sequence which comprises SEQ ID NO:1; an isolated and purified DNA which hybridizes to a DNA having a nucleotide sequence which comprises SEQ ID NO:1 under stringent conditions, and encodes a transcription factor controlling a phenylpropanoid biosynthesis pathway; a recombinant vector comprising the DNA; the recombinant vector, further comprising a promoter to which the DNA is operably fused; the recombinant vector, wherein the DNA is operably fused to the promoter in the sense or antisense direction; a plant cell into which the DNA has been introduced; a plant regenerated from the plant cell; a method of producing the plant cell, comprising introducing the DNA into the plant cell; a method of producing the plant, comprising regenerating the plant from the plant cell; an isolated and purified protein encoded by the DNA; and an isolated and purified DNA which encodes a protein having the amino acid sequence of SEQ ID NO:2.

DETAILED DESCRIPTION OF THE INVENTION

The present invention will hereinafter be described in detail.

As used herein, the term "isolated and purified" refers to a nucleic acid or protein that has been purified, i.e., separated, from the biological source that produces the biomolecule in nature.

As the stringent conditions in the present invention, 6×SSC (0.9 M NaCl, 0.09 M sodium citrate) as a buffer and a temperature of 55° C. may be used.

A phenylpropanoid biosynthesis pathway is kept widely in plants so that many plants have commonly genes relating thereto (for example, CAD gene) and also a transcription factor which controls the expression of such genes. Accordingly, the DNA of the present invention can be isolated from many plants including both herbaceous plants or woody plants by conventional methods (J. Sambrook et al., *Molecular Cloning*, 2nd ed., published by Cold Spring Harbor Laboratory Press (1989), incorporated herein by reference). The DNA of the present invention is also available by chemical synthesis in accordance with conventional methods, such as the phosphite triester method (H. Hunkapiller et al., *Nature*, 310: 105–111 (1984), incorporated herein by reference).

The DNA thus obtained is fused to the downstream region of a promoter which can express in a plant, for example, 35S promoter (CaMV35S promoter) of cauliflower mosaic virus, promoter of nopaline synthetase, promoter of a small subunit of ribulose-diphosphate-carboxylase/oxygenase, in a sense direction or anti-sense direction (J., Sambrook et al., *Molecular Cloning*, 2nd ed., published by Cold Spring Harbor Laboratory Press (1989), incorporated herein by reference). The DNA of the present invention is fused to a promoter in a sense direction in order to promote the expression of a desired gene (a gene which is the objective of promotion or suppression of expression in the present invention), while it is fused to a promoter in an anti-sense direction in order to suppress the expression of the desired gene. As another means for promoting the expression of the desired gene, it is possible to introduce, together with the DNA of the present invention fused to a promoter in a sense direction, the desired gene fused to the downstream region of another promoter into a plant cell after inserting them into one vector or to insert them separately into different vectors.

The DNA fused to a promoter can be directly introduced into a plant cell by the microinjection process, electroporation process, polyethylene glycol process, fusion process or high-speed ballistic penetration process (I. Potrykus, *Annu. Rev. Plant Physiol. Plant Mol. Biol.*, 42: 205 (1991), incorporated herein by reference). Alternatively, after being inserted into a plasmid vector for the introduction of a gene into a plant, the DNA can be indirectly introduced into a plant cell through a virus or bacteria having a plant infecting capacity (I. Potrykus, *Annu. Rev. Plant Physiol. Plant Mol. Biol.*, 42: 205 (1991), incorporated herein by reference). Examples of the virus include cauliflower mosaic virus, gemini virus, tobacco mosaic virus and brome mosaic virus. Examples of the bacteria include *Agrobacterium tumefaciens* (hereinafter referred to as "*A. timefaciens*") and *Agrobacterium rhizogenes*. For the introduction of a gene into a plant by the Agrobacterium process using *A. tumefaciens*, a plasmid such as pBI101 or pBI121 (both produced by Clontech Laboratories, Inc.) can be employed.

In the present invention, a plant wherein the expression of a desired gene has been promoted or suppressed can be obtained by proliferating or re-regenerating a plant cell into which the DNA of the present invention has been introduced by the above-described method. Conditions for proliferation or re-regeneration of such a plant cell can be selected properly, depending on the kind of the plant or the like (for example, with regard to tobacco, see R. B. Horsch et al., *Science*, 227: 1229–1231 (1985), incorporated herein by reference).

The DNA of the present invention and a vector into which the DNA has been inserted can promote or suppress the expression of a CAD gene, CHS gene, 4CL gene, PAL gene, and PRX gene. The DNA and vector according to the present invention can control the expression of not only the above-described genes but also any gene insofar as it has the above-described common sequence in its transcriptional control region.

No particular limitation is imposed on the plant in which expression of gene can be promoted or suppressed by the present invention. Essentially, plants having a phenylpropanoid biosynthesis pathway are suitable in the present invention. For example, in addition to tobacco, examples include herbaceous plants (for example, rice, arabidopsis, petunia), and woody plants (for example, poplar, eucalyptus, acacia, cedar, pine).

From genes relating to the phenylpropanoid biosynthesis pathway, a common sequence as shown in Table 1 has been found in various plant species (the numeral in the column of the common sequence indicates a distance from the transcription initiation point (unit: bp)).

TABLE 1

| Plant | Gene | Common sequence | | |
|---|---|---|---|---|
| Kidney bean | CHS1-166 | TG<u>CCACCAAACTCCTAC</u> | SEQ ID NO:3 |
| | Pal-235 | CT<u>CCACCAACCCCCTTC</u> | SEQ ID NO:4 |
| Parsley | 4CL-1632 | CTTT<u>ACCAACCCC</u>ATC | SEQ ID NO:5 |
| | Pal-193 | CT<u>CAACAAACCC</u>CTTC | SEQ ID NO:6 |
| Arabidopsis | Pal1-135 | TCT<u>CAACAACTCCT</u>CCT | SEQ ID NO:7 |
| Snapdragon | CHS-130 | TG<u>CCAACTGACCC</u>GTAG | SEQ ID NO:8 |
| Corn | C2 -175 (one of CHS) | A<u>CCCAACTAACCCC</u>GGC | SEQ ID NO:9 |
| Eucalyptus | CAD-598 | AT<u>CCAACAAAT</u>AA<u>C</u>ACA | SEQ ID NO:10 |

TABLE 1-continued

| Plant | Gene | Common sequence | |
|---|---|---|---|
| Horseradis | prxC107 | CA<u>CCACTTGAGTAC</u>AAA<br>CCAACAAACCCC<br>C T C T | SEQ ID NO:11<br>SEQ ID NO:12 |

The transcription factors bound to the common sequence in the above-described genes have almost the same structure each other and in addition, the DNAs encoding such transcription factors are considered to have a high homologous nucleotide sequence each other. The DNA according to the present invention can therefore specifically promote or suppress the expression of any one of the CAD gene, CHS gene, 4CL gene, PAL gene and PRX gene having the common sequence without depending on the plant species or the kind of the gene on which the transcription factor acts.

When the DNA of the present invention is introduced into a plant in a sense direction, the transcription factor which can bind to the common sequence of this plant is synthesized by the expression of the introduced DNA, in addition to the endogenous transcription factor. There is no limitation of the plant species into which the gene has been introduced. As a result, the expression level of the transcription factors shows an increase in total and these transcription factors are bound to the common sequence at higher frequency so that the expression of the gene that have this sequence in a promoter region is promoted.

On the other hand, when the DNA of the present invention is introduced into a plant in an anti-sense direction, RNA formed with this gene as a template is complementarily bound to mRNA derived from the gene of a transcription factor which the plant originally possesses to inhibit the synthesis of endogenous transcription factors. As a result, the expression level of transcription factors decreases, which makes it difficult to cause binding to the common sequence, so that the expression of the gene that have this sequence in a promoter region is suppressed.

The present invention also includes the isolated and purified protein encoded by SEQ ID NO:1, the amino acid sequence of which is shown as SEQ ID NO:2. Also included in the present invention is any nucleotide sequence that encodes the protein having the amino acid sequence of SEQ ID NO:2. A specific example of such a nucleotide sequence is shown in SEQ ID NO:1. Using SEQ ID NO:1 and the well-known degeneracy of the genetic code, one skilled in the art can readily deduce all of the nucleotide sequences which encode the protein having the amino acid sequence of SEQ ID NO:2. The genetic code may be found in Stryer, *Biochemistry*, Third Edition, W. H. Freeman and Company (1988), incorporated herein by reference in its entirety.

The present invention makes it possible to specifically promote or suppress the expression of a gene having a specific common sequence in its 5'-non-translated region.

In other words, the present invention makes it possible to control a gene relating to the phenylpropanoid biosynthesis pathway of a plant such as CAD gene, 4CL gene, PAL gene or PRX gene which has the common sequence.

The above-described CAD or the like is an enzyme which is involved in the phenylpropanoid biosynthesis pathway, particularly lignin biosynthesis pathway so that according to the present invention which can control the expression of the above-described genes, it becomes possible to produce trees which are promising as raw materials for paper or pulp, for example, to produce trees of a low lignin content.

The present invention will now be illustrated in greater detail with reference to Examples, but it should be understood that the present invention is not construed as being limited thereto.

EXAMPLES

Example 1

(1) Isolation and purification of tobacco mRNA

Tobacco was grown for about one month in a green house after germination from a seed and about 10 g of its leaf was ground in liquid nitrogen, and the total RNA was extracted by the method of Chomcznski et al, incorporated herein by reference.

The resulting total RNA was dissolved in sterilized water containing 0.2% diethyl dicarbonate. The resulting solution was kept at 65° C. for 5 minutes, and diluted with a twice the equivalent of a loading buffer (20 mM Tris-HCl, pH 7.6, 0.1 M NaCl, 1 mM EDTA, 0.1% SDS). The diluted solution was applied to oligo dT cellulose column which had been activated in advance. The column was washed with 5 to 10 times the column volume of a loading buffer and then with 5 times the column volume of a washing buffer (20 mM Tris-HCl, pH 7.6, 0.5 M NaCl, 1 mM EDTA, 0.1% SDS). The elution was carried out by pouring 2 to 3 times the column volume of an elution buffer (10 mM Tris-HCl, pH 7.6, 1 mM EDTA, 0.05% SDS) to the column to obtain 10 mg of purified mRNA.

(2) Preparation of cDNA library

CDNA was synthesized from mRNA obtained in (1) using an oligo dT primer in accordance with the method of Gubler & Hoffman (Gubler et al. , *Gene*, 25: 263–269 (1983)), incorporated herein by reference. The resulting cDNA was inserted into an EcoRI site of phage DNA λgt11, and in vitro packaging was carried out using λ-phage coat protein ("Gigapack II packaging extracts"; commercially available from Stratagene) to obtain a recombinant λ-phage.

On the other hand, *Escherichia coli* Y-1090 was inoculated to 10 ml of LBMM medium (1% tryptone, 1% sodium chloride, 0.5% yeast extract, 10 mM magnesium sulfate and 0.4% maltose) and precultured by shaking at 37° C. for 12 hours. After the preculture, cells were recovered by centrifugal separation, and they were suspended in 10 ml of 10 mM magnesium sulfate cooled in advance to 4° C. to make them easy to be infected with the λ-phage.

Infection was carried out by mixing the λ-phage with the resulting *Escherichia coli* and then leaving the mixture to stand at 37° C. for 15 minutes.

(3) Screening of a transcription factor

*Escherichia coli* Y-1090 infected with the recombinant λ-phage was cultured at 37° C. on LBMM medium containing 1.5% agar. About 4 hours thereafter, when the plaque-formation was observed, a nylon membrane filter ("Hybond-N"; produced by Amersham Pharmacia Biotech) which had been immersed in 10 mM isopropyl thiogalactoside (IPTG) and then air-dried in advance was placed on the culturing plate. After being left to stand overnight at 37° C., the nylon membrane filter was removed from the plate. The nylon membrane filter was then immersed at 4° C. for one hour in a binding buffer (10 mM Hepes, pH 7.5, 50 mM NaCl, 1 mM EDTA) containing 5% skimmed milk for blocking, and immersed again in the binding buffer to which a probe for binding reaction with the transcription factor blotted on the nylon membrane filter was added. The binding reaction between the probe and transcription factor was carried out at 4° C. for 2 hours.

As the probe for the bi-ding reaction, a common sequence (P-BOX sequence: -CCACTTGAGTAC-) SEQ ID NO:13 which exists in the 5'-upstream non-translated region of the 4CL gene or PAL gene of kidney bean or PRX gene of horseradish was used. That is, a double-stranded oligonucleotide having the P-BOX sequence was synthesized and it was used after labeled with digoxigenin (DIG).

After the binding reaction, the nylon membrane filter was washed three times by immersing it in a binding buffer at room temperature for 30 minutes, followed by primary screening and secondary screening by chemiluminescent detection. As a result, from $1.0 \times 10^6$ plaques, one positive plaque which was producing a protein to bind to the above-described common sequence was detected. Incidentally, in this test, the process from the labeling of the synthetic double-stranded oligonucleotide to the screening by chemiluminescent detection was mainly carried out using a commercially-available kit (produced by Boehringer Mannheim GmbH) in accordance with the non-radioisotope DIG-nucleic acid detection method.

(4) Determination of the nucleotide sequence of DNA encoding the protein to bind to the common sequence From the phage forming the above-described positive plaque, DNA was extracted in accordance with the conventional method. The inserted portion of the resulting phage DNA (in (2), the portion to which a cDNA obtained from tobacco had been inserted) was amplified by the PCR method using primers containing a cloning site of λgt11, followed by agarose gel electrophoresis, the existence of about 1 kbp DNA fragment was confirmed. After the 1 kbp DNA fragment was phosphorylated at the end thereof, it was inserted into plasmid pNoTA/T7 (PRIMER PCR CLONER™ CLONING SYSTEM (5 prime, 3 prime, Inc.) was used). Concerning the resulting recombinant plasmid DNA, the nucleotide sequence was determined using a DNA sequencer ("DNA Sequencer Model 373S", produced by Perkin Elmer Corporation) by the dideoxy method to determine the nucleotide sequence of DNA encoding the desired protein.

The sequence is represented by SEQ ID NO:1 and is presumed to be constituted by about 200 amino acids. The molecular weight is about 25 kDa. This protein is presumed to be constituted by two LIM domains, one of the zinc finger motif, based on the homology search of the protein (SWISS-PROT Rel. 34 is used as data base) If so, this transcription factor is the first example showing that an LIM domain binds to DNA. This protein was named "Ntlim1".

(5) Isolation of Ntlim1 for the confirmation of DNA binding activity.

With a view to confirming the DNA binding ability of the thus-screened protein, Ntlim1, production thereof in a necessary amount was performed using Escherichia coli.

The DNA fragment, (Ntlim1 gene) having the nucleotide sequence represented by SEQ ID NO:1 was fused to the Ntlim1 translation initiator codon region or translation terminator codon region, and amplified by the PCR method by using two primers each containing an restriction endonuclease BamHI site. After digestion of the resulting DNA fragment with restriction endonuclease BamHI, it was inserted into the BamHI site of expression plasmid pGEX-2TX (produced by Pharmacia Biotech Ltd.) and the nucleotide sequence of its junction site was studied, so that the direction of the inserted DNA and preciseness of the flame were confirmed. When Ntlim1 is produced using such a vector, it is obtained as a GST fusion protein under the control of a tac promoter.

The expression plasmid so prepared was introduced into a competent cell of Escherichia coli JM109 (produced by Toyobo Co., Ltd.) and the resulting Escherichia coli was cultured on LB agar medium (1% tryptone, 0.5% sodium chloride and 0.5% yeast extract) containing 100 mg/l of ampicillin as an antibiotic, so that a transformant with Ntlim1 gene was selected. The resulting transformant was inoculated in 1 ml of LB medium and pre-cultured overnight at 37° C. and 200 rpm. It was then subjected to shaking culture at 37° C. and 200 rpm in 30 ml of ampicillin-containing LB medium (ampicillin concentration: 100 mg/l). At the time when $OD_{600}$ became about 1.0, IPTG was added to the medium to give the final concentration of 2 mM and shaking culture was continued further at 37° C. and 100 rpm. After 5 hours, cells were recovered by centrifugal separation, and then suspended in a PBS buffer (140 mM NaCl, 2.7 mM KCl, 10.1 mM $Na_2HPO_4$, 1.8 MM $KH_2PO_4$, pH 7.3). The resulting suspension was subjected to centrifugal separation to recover the cells.

The cells so obtained were suspended in 2 ml of a PBS buffer. The suspension was subjected to ultrasonic treatment for crushing, and the supernatant (soluble fraction) was separated by centrifugal separation (15,000 g, 15 min). The soluble fraction was subjected to SDS-polyacrylamide electrophoresis to confirm the expression of the desired protein, that is, Ntlim1-GST fusion protein. The soluble fraction was then subjected to the following operations.

First, 10 μl of a 50% slurry of Glutathione Sepharose 4B (produced by Pharmacia Biotech Ltd.) was added to the fraction, followed by stirring. The mixture was then allowed to stand at room temperature for 30 minutes to allow the Ntlim1-GST fusion protein to adsorb to the Glutathione Sepharose 4B. The Glutathione Sepharose 4B having the desired protein adsorbed thereto was recovered by centrifugal separation (500 g, 5 minutes) and washed with a PBS buffer three times, and only Ntlim1 was eluted and isolated therefrom by the following steps. That is, the elution and isolation of Ntlim1 was carried out by adding 19 μl of a PBS buffer and 1 μl of thrombin protease (1 cleavage unit: an amount of enzyme, in PBS, permitting the 90% digestion of 100 μg of GST fusion protein in 16 hours) to the recovered and washed Glutathione Sepharose 4B to suspend. it, allowing the resulting suspension to stand at room temperature for 2 hours, subjecting the reaction mixture to centrifugal separation (500 g, 5 minutes) to separate the supernatant, and then subjecting the supernatant to SDS-polyacrylamide electrophoresis.

(6) Confirmation of DNA binding activity of Ntlim1

The DNA binding activity of the Ntlim1 isolated above in (5) was confirmed by the electric mobility shift assay.

In 10 μl of a binding buffer (10 mM Hepes, pH 7.5, 50 mM NaCl, 1 mM EDTA), 2 μg of the purified Ntlim1was dissolved. To the resulting solution, 10 nmol of DIG-labeled double-stranded synthetic oligonucleotide containing a P-BOX region used above in (3), and 2 μg of salmon spermatozoon DNA was added as a probe and a carrier DNA, respectively, and the resulting mixture was allowed to stand at room temperature for 20 minutes.

The reaction mixture was subjected to electrophoresis with a 5% polyacrylamide gel containing 1×TAE (6.7 mM Tris-HCl, pH 7.9, 1 mM EDTA, 3.3 mM sodium acetate) at 100 V and the electrophoresis was terminated before the free probe flew out from the gel. The electrophoresis pattern was blotted from the gel to a nylon membrane filter and chemiluminescent detection was carried out similar to (3). As a result, an electrophoresis band shifted from a position which the band of the Ntlim1 originally shows was observed and the existence of a DNA-protein complex was confirmed. On the other hand, when 1 μmol of a non-labeled probe (an utterly same probe to that used for the detection of the shifted band except that it had not been labeled with DIG) was added to the above-described reaction mixture, followed by electrophoresis under the same conditions, the shifted band had disappeared. Accordingly, it has been determined that the binding of Ntlim1 protein with P-BOX sequence is specific.

(7) Investigation of the expression-controlling activity of Ntlim1

Figure 1:
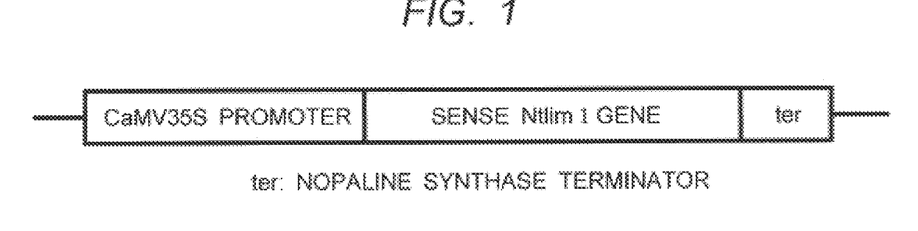
FIG. 1 is a schematic view illustrating a portion of the effector used in Example 1 into which the Ntlim1 gene has been inserted.
Figure 2:
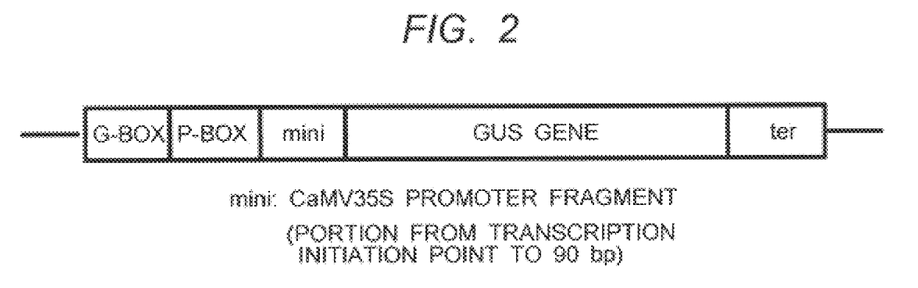
FIG. 2 is a schematic view illustrating a portion of the reporter used in Example 1 into which the P-BOX sequence-containing fused gene has been inserted.

In order to allow the Ntlim1 gene to express in a plant, a DNA fragment containing the Ntlim1 gene was inserted into the position of a β-glucuronidase gene of plasmid pBI221 (produced by Clontech Laboratories, Inc.) in a sense direction and the resulting plasmid was employed as an effector. The schematic view of a portion of the effector in which the Ntlim1 gene had been inserted is shown in FIG. 1. On the other hand, a three repeat of P-BOX sequence was ligated to the EcoRV site at −90 bp of CaMV35S promoter and a three repeat of G-BOX sequence (-CCACGTGG-), which existed commonly in the 5'-nontranslated region of a CAD gene or the like naturally (similar to the P-BOX sequence), was fused to the P-BOX sequences so as to place the G-BOX sequences upstream. The resulting fusion promoter which consisted of the G-BOX, P-BOX and CaMV35S (−90 bp) was connected to a β-glucuronidase (GUS) gene. The resulting fusion gene was inserted into pUC19 and this plasmid was used as a reporter. In this example, with a view to showing the function of the Ntlim1 gene more simply, a GUS gene whose expression could be detected very easily was placed downstream of the P-BOX sequence to be acted on by the Ntlim1 gene, instead of a CAD gene or other genes related to phenylpropanoid biosynthesis. In this case, the G-BOX sequence is presumed to act as an enhancer. The schematic view of a portion of the reporter into which the fused gene has been inserted is shown in FIG. 2.

Incidentally, each of the two recombinant plasmids prepared as described above was once introduced into a competent cell of *Escherichia coli* JM109 and amplified by culturing the *Escherichia coli*. Finally, about 1 mg of each plasmid DNA was obtained. The culture of *Escherichia coli* was carried out on LB medium, at 37° C. and a shaking rate of 200 rpm. The plasmid DNA. was isolated and purified from *Escherichia coli* by the conventional method.

In accordance with the method of Okada et al., (K. Okada et al., *Plant Cell Physiol.*, 27: 619 (1986)), incorporated herein by reference, a protoplast was prepared from tobacco culture cell BY-2. An electric pulse (200 V, 250 μF) was applied to about 3×10⁶ pieces of this protoplast suspended in 1 ml of an electroporation buffer (5 mM MES, 30 mM KCl, 0.3 M mannitol, pH 5.8) for introduction of 10 μg of the reporter or 10 μg each of the reporter and effector to the protoplasts by the electroporation method (using a gene introduction apparatus, Gene Pulser, produced by Bio-Rad Laboratories Inc.) was employed). After the protoplast subjected to gene introducing treatment was washed with 0.4 M mannitol and cultured on a protoplast medium (obtained by adding 0.4 M mannitol to a mixed salt for Murashige and Skoog medium (Nippon Shinyaku Co., Ltd.)) at 25° C. for 24 hours, it was homogenized and the soluble fraction was obtained by centrifugation. The GUS activity was measured by the method of Jefferson et al. (R. Jefferson et al., *EMBO J.*, 6: 3901–3907 (1997)), incorporated herein by reference. As a result, from the protoplast into which the reporter and effector simultaneously had been introduced, expression of the GUS gene about three times as high as that into which only the reporter had been introduced was detected. This indicates that owing to the effect of Ntlim1 (that is, a protein derived from the Ntlim1 gene of the effector), the expression of the GUS gene fused to the downstream region of the P-BOX sequence was promoted largely in the reporter. In other words, Ntlim1 is a transcription factor which binds to a P-BOX sequence and promotes the expression of a gene driven by a promoter containing P-BOX sequence. By the introduction of the Ntlim1 gene into a plant in a sense direction, the expression of the gene controlled by Ntlim1 is promoted.

Example 2

(1) Introduction of a sense or anti-sense Ntlim1 gene into tobacco

The Ntlim1 gene was inserted in a sense or anti-sense direction to a plasmid pBI121 (Clontech Laboratories, Inc.) at the position similar to that in the case of the effector prepared in (7) of Example 1. After the direction of the inserted Ntlim1 gene of the resulting recombinant plasmid was determined by a restriction endonuclease digestion test, the plasmid was introduced into *A. tumefaciens* EHA105 by the electroporation method (in 10% glycerol, an electric pulse was applied at 2500V and 25 μF). The *A. tumefaciens* was cultured on LB medium containing 100 mg/l of kanamycin at 28° C. for 2 days and only those into which the recombinant plasmid has been introduced were selectively obtained.

Tobacco (*Nicotiana tabacum* L cv. SR-1) was used as a plant into which an Ntlim1 gene had been introduced. That is, a leaf of the seedling which was grown in sterile conditions (about 4 weeks-old after germination) was cut into 5 mm square, and immersed for 1 to 3 minutes in a culture solution of the recombinant plasmid-introduced *A. tumefacines* with the epidermis side of the leaf discs down to infect them with *A. tumefaciens* so that the Ntlim1 gene was introduced into the leaf discs. After the removal of the culture solution attached thereto by a sterilized paper towel or the like, the infected leaf discs were placed on a callus induced medium (Murashige and Skoog basic medium, 3% sucrose, 0.25% gellan gum, 1 mg/l naphthalene acetic acid, 0.1 mg/l benzyladenine) and cultured for 3 days under the continuous illumination at 25° C. The cultured discs were then transferred to a medium for shoot. formation (Murashige and Skoog basic medium, 3% sucrose, 0.25% gellan gum, 0.1 mg/l naphthalene acetic acid, 1 mg/l benzyladenine, 100 mg/l kanamycin, 500 mg/l carbenicillin) and cultured at the same temperature under the same optical conditions as described above to differentiate shoots.

The differentiated shoots were cut about 4 weeks after the culturing on a medium for shoot formation, transferred to Murashige and Skoog basic medium (3% sucrose, 0.8% agar or 0.25% gellan gum was added) containing 100 mg/l of kanamycin and 500 mg/l of carbenicillin and was allowed to induce root by culturing for about 4 weeks at the same temperature under the same optical conditions as described above. The rooting plant was grown in a green house at 25° C. by using Metromix 350 (produced by Scotts-Sierra Horticulture Company) as a culture soil.

(2) Analysis of transformed tobacco with the Ntlim1 gene
 (2-1) Analysis by PCR

The genomic DNA was extracted from the transformant tobacco leaves grown in (1) in accordance with the conventional method, and PCR was carried out by using an oligonucleotide corresponding to the nucleotide sequence in the Ntlmi1 gene as a primer. As a result, from any one of PCR samples, amplification of the Ntlim1 gene was detected and it was confirmed that 25 transformants provided for analysis had a sense or anti-sense Ntlim1 gene (of which 13 individuals were sense transformants and 12 individuals were anti-sense transformants).

(2-2) Analysis by Northern hybridization

From the transformant tobacco (8 week old) in which the existence of the Ntlim1 gene had been confirmed in (2-1), two sense transformants (to which the Ntlim1 gene had been introduced in the sense direction) and two anti-sense transformants (to which the Ntlim1 gene had been introduced in the anti-sense direction) were selected. From their stems, total RNA was extracted by the acid guanidine phenol chloroform method. As a control, the total RNA was also extracted from non-transformed tobacco at the same time.

A 10 µg portion of the total RNA so extracted was fractionated by electrophoresis at 60 V for 2 hours by using 1.2% agarose gel containing formaldehyde of 0.66 M in a final concentration and 1×MOPS buffer (20 mM MOPS/pH 7.0, 5 mM sodium acetate, 0.5 mM EDTA). After electrophoresis, the electrophoresis pattern was blotted from the gel to a nylon membrane filter and the resulting nylon membrane filter was subjected to Northern hybridization.

Figure 3:
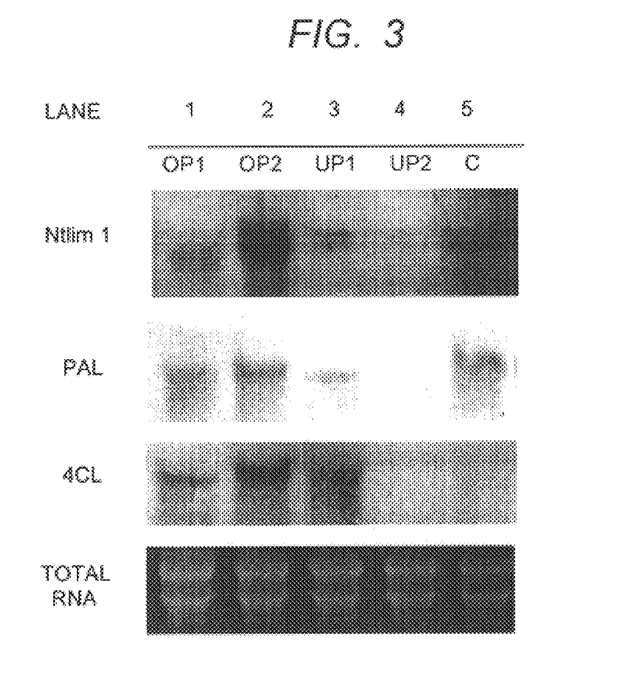
FIG. 3 illustrates the expression of each gene in tobacco into which the Ntlim1 gene has been introduced in a sense or anti-sense direction.

The Northern hybridization was carried out as in Example 1(3) in accordance with the non-radioisotope DIG-nucleic acid detection method by using, in addition to the Ntlim1 gene, a PAL gene (820 bp) and a 4CL gene (610 bp), which had been obtained by the amplification of the genomic DNA of tobacco by the PCR method, as probes. FIG. 3 shows the results of chemiluminescence of the above-described nylon membrane filter after Northern hybridization.

From FIG. 3, it has been found that the expression of the Ntlim1 gene in the transformant was stronger in the sense transformants OP1 and OP2 (lanes 1 and 2) and weaker in the anti-sense transformants UP1 and UP2 (lanes 3 and 4), than that in a non-transformant C (lane 5). Concerning the sense transformants OP1 and OP2, stronger expression was recognized in both of the PAL gene and 4CL gene than that in the non-transformant C and this tendency was particularly eminent in the OP2. On the other hand, expression of each of the PAL gene and 4CL gene was almost completely inhibited in the anti-sense transformant UP2. In the anti-senses transformant UP1, the expression of each of the PAL gene and 4CL gene was not suppressed so much, presumably because the introduction amount of the anti-sense gene in this transformant (in the anti-sense transformant UP2 whose expression of PAL gene or 4CL gene has been almost completely inhibited, many copies of the anti-sense gene of Ntlim1 are presumed to be introduced into a plant genome) or effect of the position of the anti-sense gene in the plant genome is presumed to have a large influence.

From the above-described results, it becomes apparent that the Ntlim1 gene, that is, the DNA according to the present invention, can promote or suppress the expression of the PAL gene or 4CL gene. In addition, the transcription factor synthesized from the DNA of the present invention functions by binding to the P-BOX of such genes or to the common sequence of the 5'-non-translated region analogous to the P-BOX so that it can exhibit promotion effects on not only the above-described PAL gene or 4CL gene, but also any kind of a gene insofar as it has such a common sequence.

While the invention has been described in detail and with reference to specific examples thereof, it will be apparent to one skilled in the art that various changes and modifications can be made therein without departing from the spirit and scope thereof.

The priority application, Japanese patent application No. Hei 10-125171, filed Mar. 31, 1998, is incorporated herein by reference in its entirety.

What is claimed is:

1. An isolated and purified DNA having a nucleotide sequence which comprises SEQ ID NO:1.

2. The DNA of claim 1, having a nucleotide sequence which consists of SEQ ID NO:1.

3. A recombinant vector comprising the DNA of claim 1.

4. The recombinant vector of claim 3, further comprising a promoter to which the DNA is operably fused.

5. The recombinant vector of claim 4, wherein the DNA is operably fused to the promoter in the sense direction.

6. The recombinant vector of claim 4, wherein the DNA is operably fused to the promoter in the antisense direction.

7. A transgenic plant cell into which the DNA of claim 1 has been introduced.

8. A transgenic plant regenerated from the plant cell of claim 7.

9. An isolated and purified DNA which encodes a protein having the amino acid sequence of SEQ ID NO:2.

* * * * *

SEQUENCE LISTING

```
<160> NUMBER OF SEQ ID NOS: 13

<210> SEQ ID NO 1
<211> LENGTH: 988
<212> TYPE: DNA
<213> ORGANISM: Nicotiana tabacum
<220> FEATURE:
<221> NAME/KEY: CDS
<222> LOCATION: (100)..(702)
<220> FEATURE:
<221> NAME/KEY: misc_feature
<222> LOCATION: (127)..(282)
<223> OTHER INFORMATION: LIM domain
<220> FEATURE:
<221> NAME/KEY: misc_feature
<222> LOCATION: (427)..(582)
<223> OTHER INFORMATION: LIM domain

<400> SEQUENCE: 1
gaattcgcgg ccgttccaaa aaccaagtgc taacacaaag aaagggaaag agccacaaag         60
accatttttg ttttctgtaa aacttgctcg tatatagcc atg gct ttt gca gga        114
                                            Met Ala Phe Ala Gly
                                             1               5 acc aca cag aaa tgc atg gca tgt gac aag act gtc tat ctg gtt gac       162
Thr Thr Gln Lys Cys Met Ala Cys Asp Lys Thr Val Tyr Leu Val Asp
         10                  15                  20
```

```
aaa tta act gca gat aac aga atc tat cac aaa gct tgt ttc aga tgc      210
Lys Leu Thr Ala Asp Asn Arg Ile Tyr His Lys Ala Cys Phe Arg Cys
             25                  30                  35 cat cac tgc aag ggc act gtc aag ctt ggc aac tac aat tcc ttt gag      258
His His Cys Lys Gly Thr Val Lys Leu Gly Asn Tyr Asn Ser Phe Glu
         40                  45                  50 gga gtt cta tac tgt aga cca cac ttt gat cag ctc ttc aaa caa act      306
Gly Val Leu Tyr Cys Arg Pro His Phe Asp Gln Leu Phe Lys Gln Thr
     55                  60                  65 ggc agt ttg gat aaa agc ttt gaa ggt aca cca aaa aat gtg aag cca      354
Gly Ser Leu Asp Lys Ser Phe Glu Gly Thr Pro Lys Asn Val Lys Pro
 70                  75                  80                  85 cag aaa ccc att gac agt gag aaa cca cag gta gcc aaa gtg aca agc      402
Gln Lys Pro Ile Asp Ser Glu Lys Pro Gln Val Ala Lys Val Thr Ser
                 90                  95                 100 atg ttt ggt gga aca aga gag aaa tgt ttt ggc tgc aag aaa act gtc      450
Met Phe Gly Gly Thr Arg Glu Lys Cys Phe Gly Cys Lys Lys Thr Val
             105                 110                 115 tac cca aca gaa aag gta tca gcc aat ggc acg cca tac cat aag agc      498
Tyr Pro Thr Glu Lys Val Ser Ala Asn Gly Thr Pro Tyr His Lys Ser
         120                 125                 130 tgc ttc caa tgc agc cac gga ggc tgt gta ata agc cct tcc aac tat      546
Cys Phe Gln Cys Ser His Gly Gly Cys Val Ile Ser Pro Ser Asn Tyr
     135                 140                 145 acc gca cat gag ggg cgc tta tat tgt aaa cat cac cat att caa ctt      594
Thr Ala His Glu Gly Arg Leu Tyr Cys Lys His His His Ile Gln Leu
150                 155                 160                 165 atc aag gag aag ggc aac tta agc aag ctt gag ggt gac cat gaa atg      642
Ile Lys Glu Lys Gly Asn Leu Ser Lys Leu Glu Gly Asp His Glu Met
                 170                 175                 180 aat tcc acg aca aca aca gga gtt act gca gag tca tac aca gcc gac      690
Asn Ser Thr Thr Thr Thr Gly Val Thr Ala Glu Ser Tyr Thr Ala Asp
             185                 190                 195 caa gtt gat tga tccttatctt taccgcgatc atgtattacg tatctgctgt          742
Gln Val Asp
         200 tagttgtaag aatcgaaggc gttcagcagc ttccatgaat gcacttgcct tgccccagcg    802 tatgttttac tctaatctag cttcaattaa tttgatgttg aactatatat tgtctagctt    862 ttgtgtgtag attttgacc tttgtttgct tgtgcttcac ttgtattatg tgaatgttga     922 atgagattga ataaacatg gttttgctgt cccagtgcat gcaaatcttt gagcggccgc     982 gaattc                                                                988

<210> SEQ ID NO 2
<211> LENGTH: 200
<212> TYPE: PRT
<213> ORGANISM: Nicotiana tabacum

<400> SEQUENCE: 2

Met Ala Phe Ala Gly Thr Thr Gln Lys Cys Met Ala Cys Asp Lys Thr
 1               5                  10                  15

Val Tyr Leu Val Asp Lys Leu Thr Ala Asp Asn Arg Ile Tyr His Lys
             20                  25                  30

Ala Cys Phe Arg Cys His His Cys Lys Gly Thr Val Lys Leu Gly Asn
         35                  40                  45

Tyr Asn Ser Phe Glu Gly Val Leu Tyr Cys Arg Pro His Phe Asp Gln
     50                  55                  60

Leu Phe Lys Gln Thr Gly Ser Leu Asp Lys Ser Phe Glu Gly Thr Pro
```

```
        65                    70                    75                    80
Lys Asn Val Lys Pro Gln Lys Pro Ile Asp Ser Glu Lys Pro Gln Val
                    85                    90                    95

Ala Lys Val Thr Ser Met Phe Gly Gly Thr Arg Glu Lys Cys Phe Gly
            100                   105                   110

Cys Lys Lys Thr Val Tyr Pro Thr Glu Lys Val Ser Ala Asn Gly Thr
        115                   120                   125

Pro Tyr His Lys Ser Cys Phe Gln Cys Ser His Gly Gly Cys Val Ile
    130                   135                   140

Ser Pro Ser Asn Tyr Thr Ala His Glu Gly Arg Leu Tyr Cys Lys His
145                   150                   155                   160

His His Ile Gln Leu Ile Lys Glu Lys Gly Asn Leu Ser Lys Leu Glu
                165                   170                   175

Gly Asp His Glu Met Asn Ser Thr Thr Thr Gly Val Thr Ala Glu
            180                   185                   190

Ser Tyr Thr Ala Asp Gln Val Asp
        195                   200

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
tgccaccaaa ctcctac                                                       17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
ctccaccaac ccccttc                                                       17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ctttaccaac ccccatc                                                       17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
ctccaacaaa cccttc                                                        17
```

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
tctcaacaac tcctcct                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
tgccaactga cccgtag                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
acccaactaa ccccggc                                                    17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
atccaacaaa taacaca                                                    17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
caccacttga gtacaaa                                                    17

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ccaacaaacc cc                                                         12

<210> SEQ ID NO 13

-continued

```
<211> LENGTH: 12
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
ccacttgagt ac                                                          12
```